United States Patent [19]

Righton

[11] Patent Number: 5,935,916
[45] Date of Patent: Aug. 10, 1999

[54] METHOD FOR THE MANUFACTURE OF A CLEANSING PRODUCT

[75] Inventor: Abigail Righton, West Wittering, United Kingdom

[73] Assignee: The Body Shop International Plc., West Sussex, United Kingdom

[21] Appl. No.: 09/143,372

[22] Filed: Aug. 28, 1998

Related U.S. Application Data

[62] Division of application No. 08/734,449, Oct. 17, 1996, Pat. No. 5,801,134, which is a continuation of application No. 08/499,914, Jul. 11, 1995, abandoned.

[30] Foreign Application Priority Data

Jul. 12, 1994 [GB] United Kingdom .................. 9413981

[51] Int. Cl.$^6$ ........................................ C11D 11/00
[52] U.S. Cl. ........................ 510/130; 510/141; 510/145; 510/403; 510/462; 510/463; 510/466
[58] Field of Search ................... 510/130, 141, 510/145, 403, 462, 463, 466

[56] References Cited

U.S. PATENT DOCUMENTS

| | | | |
|---|---|---|---|
| 2,356,903 | 8/1944 | Wood | 510/156 |
| 2,560,097 | 7/1951 | Emerson, Jr. et al. | 510/156 |
| 2,845,391 | 7/1958 | Searle | 510/156 |
| 3,129,187 | 4/1964 | Meehan | 510/156 |
| 3,248,333 | 4/1966 | O'Roark | 510/156 |
| 3,689,437 | 9/1972 | McLaughlin | 510/158 |
| 4,100,097 | 7/1978 | O'Roark | 510/156 |
| 4,151,105 | 4/1979 | O'Roark | 510/151 |
| 4,424,234 | 1/1984 | Alderson et al. | 424/317 |
| 4,439,355 | 3/1984 | Kenkare | 510/145 |
| 4,941,990 | 7/1990 | McLaughlin | 510/151 |
| 4,976,953 | 12/1990 | Orr et al. | 424/47 |
| 5,013,473 | 5/1991 | Norbury et al. | 424/452 |
| 5,171,151 | 12/1992 | Barthold | 434/82 |
| 5,182,103 | 1/1993 | Nakane et al. | 424/78.03 |
| 5,227,086 | 7/1993 | Kacher et al. | 510/146 |
| 5,262,079 | 11/1993 | Kacher et al. | 510/146 |
| 5,264,144 | 11/1993 | Moroney et al. | 510/151 |
| 5,264,145 | 11/1993 | French et al. | 510/151 |
| 5,385,685 | 1/1995 | Humpherys et al. | 510/119 |
| 5,389,279 | 2/1995 | An et al. | 510/126 |
| 5,425,892 | 6/1995 | Taneri et al. | 510/146 |

FOREIGN PATENT DOCUMENTS

| | | |
|---|---|---|
| 0370969 | 11/1989 | European Pat. Off. . |
| 5-3053438 | 10/1976 | Japan . |
| 62-164799 | 7/1987 | Japan . |
| 678063 | 7/1991 | Switzerland . |

*Primary Examiner*—Lorna Douyon
*Attorney, Agent, or Firm*—Banner & Witcoff, Ltd.

[57] ABSTRACT

A method of making a solid malleable non-hardenable cleansing product for personal use having a plasticine like consistency comprising 35% to 80% by weight of powder material, such as Kaolin, 10% to 25% by weight of surfactant material and 5% to 28% by weight of anhydrous base material to give a pH neutral, vegetarian, soap-free product.

6 Claims, No Drawings

METHOD FOR THE MANUFACTURE OF A CLEANSING PRODUCT

This application is a divisional of U.S. application Ser. No. 08/734,449, filed Oct. 17, 1996, now U.S. Pat. No. 5,801,134 which was a continuation of U.S. application Ser. No. 08/499,914, filed Jul. 11, 1995, now abandoned, each application of which is herein incorporated by reference in its entirety.

FIELD OF THE INVENTION

This invention relates to a cleansing product for personal use.

BACKGROUND OF THE INVENTION

It is known to provide cleansing products for personal use, usually referred to as soaps, in either the form of a solid cake or in the form of a liquid or gel.

Attempts have been made to form kneadable cleansing products. One known form of kneadable soap is based on a gelatin matrix made malleable by the addition of paraffin or mineral oils. Such a product is, however, not suitable for many applications, being neither vegetarian not free of mineral oils, and harsh on delicate skins. Further malleable soaps have been made which remedy this harshness but these cleansing agents must be kept moist to remain malleable.

SUMMARY OF THE INVENTION

The present invention seeks to provide an alternative form of non-hardenable malleable cleansing product, or soap, which is attractive to young children.

According to the present invention there is provided a cleansing product for personal use in the form of a solid composition with a plastic consistency, the composition comprising 35% to 80% by weight of powder material, 10% to 25% by weight of surfactant material and 5% to 28% by weight of anhydrous base material.

A method for the manufacture of a cleansing product for personal use in the form of a solid composition with a plastic consistency, wherein the composition comprises 35% to 80% by weight of powder material, 10% to 25% by weight of surfactant material, and 5% to 28% by weight of anhydrous base material, the method comprising the following steps:

sieving the powder material and then blending the powder material in a powder mixer/blender until a homogenous powder phase is formed;

separately melting the anhydrous base material to form a molten phase, adding fragrance and preservatives to the molten phase, and then blending the molten phase by stirring;

combining the surfactant material and the molten phase, blending, and then adding the homogenous powder phase;

mixing the surfactant material, molten phase, and homogenous powder phase in a blending machine until homogenous and to fully form a plastic, moldable texture.

DETAILED DESCRIPTION OF THE INVENTION

The powder material preferably consists of one or more of natural or synthetic hydrated aluminium silicate, metallic oxides, magnesium silicate, silicate minerals, vegetable starches, plant fines, synthetic polymer powders, calcium carbonate, cellulose and cellulose derivatives.

The surfactant material preferably consists of one or more of an anionic, nonionic or amphoteric surfactant. The anhydrous base material may comprise one or more of plant oils/waxes/butters; synthetic waxes/butters, hydrogenated oils, fatty esters, fatty alcohols, sorbitol esters, lanolin, lanolin derivatives, silicone waxes, silicone oils, silicone copolymers.

The product may further contain one or more of the following:—water, dyestuff, pigments, UV absorbers, antioxidants, fragrance, preservatives, humectants, vitamins, plant extracts, glycols, skin conditioning agent and bittering additives.

A preferred composition for the cleansing product is approximately 60% by weight of Kaolin, 20% by weight of Sodium Laureth Sulphate, 15% to 19% of an anhydrous base material comprising a texturizer in the form of Vegetable Starch and Bis-Diglyceryl Fatty Ester Adipate and small percentages of preservatives, colorants and fragrance. Preferably, the Kaolin, Vegetable Starch, and some at least of the preservatives and pigments are in powder form.

A preferred method of manufacture comprises the following steps:

1. The dye solutions are diluted by dissolving in water in an approximate ratio of 5 parts of dye solution to 100 parts of water.

2. The dye solutions are then combined with the cleansing agent, Sodium Laureth Sulphate to form a surfactant phase.

3. The powder ingredients, that is, the Vegetable Starch, which has been already subjected to a sieving operation, the Kaolin, the powder preservatives and pigments are then blended in a powder mixer/blender until a homogenous powder phase is formed.

4. The texturizer in the form of the Bis-Diglyceryl Fatty Ester Adipate is separately melted and, whilst in the molten phase, fragrance and further preservatives are added, the mix being blended by stirring, to form a molten phase.

The surfactant phase and the molten phase are added to the homogenous powder in a blending machine and the composition is mixed until the batch is homogenous and the desired plastic, moldable, texture is fully formed.

The bulk material is then extruded or molded into a final desired shape prior to packaging and labeling.

In a modified method of manufacture for the product, the powder materials comprising Kaolin, Vegetable Powder, preservatives and pigments are mixed with dispersion to form a powder phase which is homogenous, smooth and uniform.

Dye solutions are prepared by dissolving dye in water in an approximate ratio of 5 to 100 parts by weight in liquid form and are then added to the powder phase. Mixing is continued until the combined ingredients are completely uniform and homogenous.

Texturizer in the form of Bis-Diglyceryl Fatty Ester Adipate is separately melted by heating to a temperature of 55° C. to 60° C. to form a molten phase.

The molten phase and the surfactant/cleansing agent which is in the form of an aqueous paste, are then mixed with the mix of the powder phase and the dyes without dispersion until a dough-like or plasticine-like texture forms and the bulk material is smooth, uniform and homogenous.

The finished bulk is then extruded and/or molded into the desired shape ready for packaging and labeling.

Products formed in accordance with the present invention and which may be manufactured by the above processes have the following advantages:

1. can be used when wetted or dry for polymorphic modeling;

2. can be used for topical body cleansing when wetted, during which application a lather or foam is produced;

3. is suitable for vegetarians;

4. is soap-free and petrolatum free;

5. has a pH close to neutral (7.0–7.5) in contrast to conventional soaps which have a high pH (>9.0).

I claim:

1. A method for the manufacture of a cleansing product for personal use in the form of a solid composition with a plastic consistency, wherein the composition comprises 35% to 80% by weight of powder material, 10% to 25% by weight of surfactant material, and 5% to 28% by weight of anhydrous base material selected from the group consisting of plant oils, plant waxes, plant butters, synthetic waxes, synthetic butters, hydrogenated oils, fatty esters, fatty alcohols, sorbitol esters, lanolin, lanolin derivatives, silicone waxes, silicone oils, silicone copolymers and mixtures thereof, and wherein the composition is soap-free and contains no gelatin, paraffin or mineral oil, the method comprising the following steps:

sieving the powder material and then blending the powder material in a powder mixer/blender until a homogenous powder phase is formed;

separately melting the anhydrous base material to form a molten phase, adding fragrance and preservatives to the molten phase, and then blending the molten phase by stirring;

combining the surfactant material and the molten phase, blending, and then adding the homogenous powder phase;

mixing the surfactant material, molten phase, and homogenous powder phase in a blending machine until homogenous and to fully form a finished bulk having a plastic, moldable texture.

2. The method of claim 1:

wherein the powder phase is mixed with a dye solution prepared by dissolving dye in water in an approximate ratio of 5 to 100 parts by weight in liquid form, to form a uniform and homogenous dye/powder phase;

wherein the anhydrous base material comprises a texturizer which is heated to a temperature of 55° C. to 60° C. to form the molten phase;

wherein the molten phase is combined with the surfactant, and then mixed with the dye/powder phase to form a smooth, homogenous, finished bulk having a dough or plastic, moldable texture.

3. The method of claim 1 wherein the finished bulk is then molded into the desired shape ready for packaging and labeling.

4. The method of claim 2 further comprising molding the finished bulk into the desired shape ready for packaging and labeling.

5. The method of claim 2 wherein the powder material comprises Kaolin, Vegetable Powder, and pigments; and the texturizer is Bis-Diglyceryl Fatty Ester Adipate.

6. The method of claim 2 wherein the surfactant is in the form of an aqueous paste.

* * * * *

UNITED STATES PATENT AND TRADEMARK OFFICE
CERTIFICATE OF CORRECTION

PATENT NO.: 5,935,916

DATED: August 10, 1999

INVENTOR(S): Abigail RIGHTON

It is certified that an error appears in the above-identified patent and that said Letters Patent is hereby corrected as shown below:
Title page;

In item [30] Foreign Application Priority Data:

Delete "9413981" and insert --9413981.3--.

Signed and Sealed this

Sixth Day of June, 2000

*Attest:*

Q. TODD DICKINSON

*Attesting Officer*  *Director of Patents and Trademarks*